United States Patent
Stock et al.

(10) Patent No.: US 8,563,787 B2
(45) Date of Patent: Oct. 22, 2013

(54) PREPARATION OF HOMOALLYL ALCOHOLS IN THE PRESENCE OF NONCOVALENTLY SUPPORTED IONIC LIQUID PHASE CATALYSTS UNDER GAS-PHASE REACTION CONDITIONS

(75) Inventors: Christoph Stock, Ellerstadt (DE); Dirk Gerhard, Mannheim (DE); Klaus Ebel, Lampertheim (DE)

(73) Assignee: BASF SE, Ludwigshafen (DE)

( * ) Notice: Subject to any disclaimer, the term of this patent is extended or adjusted under 35 U.S.C. 154(b) by 199 days.

(21) Appl. No.: 13/252,386

(22) Filed: Oct. 4, 2011

(65) Prior Publication Data

US 2012/0083630 A1 Apr. 5, 2012

Related U.S. Application Data

(60) Provisional application No. 61/389,738, filed on Oct. 5, 2010.

(51) Int. Cl.
*C07C 29/38* (2006.01)

(52) U.S. Cl.
USPC ........................................................ 568/881

(58) Field of Classification Search
USPC ........................................................ 568/881
See application file for complete search history.

(56) References Cited

U.S. PATENT DOCUMENTS

| 4,511,751 A | 4/1985 | Ninagawa et al. |
| 2008/0028777 A1 | 2/2008 | Boesmann et al. |
| 2008/0269477 A1 | 10/2008 | Stegmann et al. |

FOREIGN PATENT DOCUMENTS

| GB | 2451046 A | 1/2009 |
| WO | WO-03/029329 A2 | 4/2003 |
| WO | WO-2005/113702 A1 | 12/2005 |
| WO | WO-2006/000197 A1 | 1/2006 |
| WO | WO-2007/076979 A1 | 7/2007 |
| WO | WO-2007/128268 A2 | 11/2007 |
| WO | WO-2008/043837 A1 | 4/2008 |

OTHER PUBLICATIONS

International Search Report for PCT/EP2011/067244, mailing date Feb. 15, 2012.

Jyothi, et al., "A Lewis Acid Catalyst Anchored on Silica Grafted with Quaternary Alkylammonium Chloride Moieties", *Angew. Chem. Int. Ed.*, vol. 40, No. 15, (2001), p. 2881-2884.

Rashinkar, et al., "An expeditious synthesis of homoallylic alcohols using Bronsted acidic supported ionic liquid phase catalyst with pendant ferrocenyl group", *Catalysis Communications*, vol. 12, (2011), p. 1442-1447.

Van Doorslaer, et al., "Immobilization of molecular catalysts in supported ionic liquid phases", *Dalton Trans.*, vol. 39, (2010), p. 8377-8390.

Xuefeng, et al., "Synthesis of 3-Methylbut-3-en-1-ol over Immobilized SnCl4 Catalyst", *Petrochemical Techonology*, vol. 39, No. 8, (2010), p. 909-912.

*Primary Examiner* — Elvis O Price

(74) *Attorney, Agent, or Firm* — Novak Druce Connolly Bove + Quigg LLP

(57) ABSTRACT

Process for preparing homoallyl alcohols by catalyzed reaction of alkenes with aldehydes or ketones, wherein the reaction is carried out in the gas phase in the presence of noncovalently supported ionic liquid phase catalysts.

10 Claims, No Drawings

PREPARATION OF HOMOALLYL ALCOHOLS IN THE PRESENCE OF NONCOVALENTLY SUPPORTED IONIC LIQUID PHASE CATALYSTS UNDER GAS-PHASE REACTION CONDITIONS

CROSS-REFERENCE TO RELATED APPLICATION

This application claims the benefit of U.S. Provisional Application Ser. No. 61/389,738 filed Oct. 5, 2010, the entire contents of which are incorporated herein by reference in its entirety.

FIELD OF THE INVENTION

The invention relates to the selective preparation of homoallyl alcohols from alkenes and aldehydes or ketones in the presence of noncovalently supported ionic liquid phase catalysts under gas-phase reaction conditions.

BACKGROUND

Homoallyl alcohols can be prepared, for example, by a reaction known as the Prins reaction, which generally refers to the electrophilic addition of an aldehyde or ketone onto an alkene followed by addition of a nucleophile onto the resulting intermediate. An ene reaction is also possible for this purpose; this is generally known as a pericyclic reaction in which an alkene bearing a hydrogen in the allylic position is reacted with a compound having a multiple bond. It proceeds with increased difficulty, the higher the degree of substitution in the allylic position which bears the proton to be transferred.

The prior art is summarized below:

*JACS* 1955, 77, 4666-8 describes the uncatalyzed thermal addition of paraformaldehyde onto dialkyl-substituted terminal olefins under superatmospheric pressure and elevated temperature. Specifically, the conversion of isobutene into 3-methyl-3-buten-1-ol is described and the influence of various reaction conditions is indicated.

*JACS* 1982, 104, 555-63 discloses the catalyzed Prins reaction of aldehydes. A general problem associated with ene reactions of aldehydes (paraformaldehyde) catalyzed by a Lewis acid is said to be the alcohol-Lewis acid complex formed, which is sensitive to solvolysis. In addition, it is a strong protic acid which can protonate the double bond.

U.S. Pat. No. 4,511,751 describes the reaction of isobutene and/or tertiary butanol with formaldehyde in an acidic aqueous solution. Since the alcohol function is eliminated, the reaction product (at temperatures >150° C.) is not the unsaturated alcohol isoprenol but isoprene.

*Chem. Commun.* 2001, 992-3 teaches that the direct immobilization of catalysts on inorganic support materials can be disadvantageous because decreases in activity can occur because of leaching. As an alternative, it is indicated that the metal catalyst ($SnCl_4$) can be anchored via tetraalkylammonium chloride on the support (MCM-41) and the activity could be retained in this way. The cation is covalently bound to the surface of the support via a siloxane function; this chemical fixing makes a plurality of chemical reactions necessary. Reactions of isobutene with paraformaldehyde in a nonaqueous medium have confirmed the hypothesis.

According to *Angew. Chem. Int. Ed.* 2005, 44, 815-9, SILP (supported ionic liquid phase) catalyst systems can be used for olefin hydroformylation (Rh-catalyzed), hydrogenation (Rh-catalyzed), Heck reactions (Pd-catalyzed) and hydroamination (Rh-, Pd- and Zn-catalyzed). The INV0070434 MST/Ya Apr. 8, 2011 0 FIG./0 Seq transition metal complexes are here dissolved in a thin film of ionic liquid which is held on a porous solid having a large surface area by physisorption or else by covalent anchoring.

BRIEF SUMMARY

It was an object of the invention to prepare homoallyl alcohols selectively by reaction of alkenes with aldehydes or ketones under mild reaction conditions, e.g. atmospheric pressure. A catalyst suitable for this purpose was to be found. Such a reaction should advantageously be able to take place in the presence of water since formaldehyde is frequently used as starting material and is inexpensive in aqueous form. The process should advantageously be able to be carried out continuously, which makes it necessary for the catalyst activity to be maintained. Furthermore, a high space time yield is desirable.

The object is achieved by a process for preparing homoallyl alcohols by catalyzed reaction of alkenes with aldehydes or ketones, wherein the reaction is carried out in the gas phase in the presence of noncovalently supported ionic liquid phase catalysts. It is advantageous that the catalyst retains its activity and thus makes a continuous reaction possible. It is particularly advantageous that the preparative process found allows the presence of water.

It was surprising that a high selectivity is achieved in the reaction of, for example, olefins with aqueous formaldehyde to form homoallyl alcohol when using the SILP (supported ionic liquid phase) technology. In addition, it has been found that the supported ionic liquid phase system is maintained in an active state during the reaction. Reaction in the gas phase enables olefin which has been used in excess and has not been consumed to be recirculated to the reaction. It is possible to carry out the reaction under atmospheric pressure.

DETAILED DESCRIPTION OF THE PREFERRED EMBODIMENTS

The catalyst system employed will be described below:

For the present purposes, the term ionic liquids refers to salts (compounds made up of cations and anions) which at atmospheric pressure (1 bar) have a melting point of <350° C., preferably <300° C., particularly preferably <250° C. and very particularly preferably <100° C. In a particularly preferred embodiment, the ionic liquids are liquid at the reaction temperature under atmospheric pressure (1 bar).

Preferred ionic liquids comprise an organic compound as cation (organic cation). Depending on the valence of the anion, the ionic liquid can comprise further cations, including metal cations, in addition to the organic cation. The cations or particularly preferred ionic liquids are exclusively an organic cation or, in the case of polyvalent anions, a mixture of identical or different organic cations.

Suitable organic cations are, in particular, organic compounds having heteroatoms such as nitrogen, sulfur, oxygen or phosphorus; the organic cations are in particular compounds having an ammonium group (ammonium cations), an oxonium group (oxonium cations), a sulfonium group (sulfonium cations) or a phosphonium group (phosphonium cations).

In a particular embodiment, the organic cations of the ionic liquids are ammonium cations. These are, in particular, non-aromatic compounds having a localized positive charge on the nitrogen atom. They can be, for example, compounds having tetravalent nitrogen (quaternary ammonium compounds) or compounds having trivalent nitrogen, with one bond being a double bond, or aromatic compounds having a delocalized positive charge and at least one nitrogen atom, preferably one or two nitrogen atoms, in the aromatic ring system.

Preferred organic cations are quaternary ammonium cations having preferably three or four aliphatic substituents, particularly preferably $C_1$-$C_{12}$-alkyl groups, which may optionally be substituted by hydroxyl groups, on the nitrogen atom. Particular preference is given to organic cations which comprise a heterocyclic ring system having one or two nitrogen atoms as constituent of the ring system. Monocyclic, bicyclic, aromatic or nonaromatic ring systems are possible. Mention may be made by way of example of bicyclic systems as are described in WO 2008/043837. These bicyclic systems are diazabicyclo derivatives, preferably composed of a 7-membered ring and a 6-membered ring, which comprise an amidinium group; particular mention may be made of the 1,8-diazabicyclo[5.4.0]undec-7-enium cation. Very particularly preferred organic cations comprise a five- or six-membered heterocyclic ring system having one or two nitrogen atoms as constituent of the ring system. Possible organic cations of this type are, for example, pyridinium cations, pyridazinium cations, pyrimidinium cations, pyrazinium cations, imidazolium cations, pyrazolium cations, pyrazolinium cations, imidazolinium cations, thiazolium cations, triazolium cations, pyrrolidinium cations and imidazolidinium cations. These cations are, for example, listed in WO 2005/113702. If it is necessary to obtain a positive charge on the nitrogen atom or in the aromatic ring system, the nitrogen atoms are in each case substituted by an organic group which in general has not more than 20 carbon atoms, preferably a hydrocarbon group, in particular a $C_1$-$C_{16}$-alkyl group, in particular a $C_1$-$C_{10}$-alkyl group, particularly preferably a $C_1$-$C_4$-alkyl group.

The carbon atoms of the ring system can also be substituted by organic groups which generally have not more than 20 carbon atoms, preferably a hydrocarbon group, in particular a $C_1$-$C_{16}$-alkyl group, in particular a $C_1$-$C_{10}$-alkyl group, particularly preferably a $C_1$-$C_4$-alkyl group.

Particularly preferred ammonium cations are quaternary ammonium cations, imidazolium cations, pyrimidinium cations and pyrazolium cations. Very particular preference is given to imidazolium cations, in particular cations described by the formula I below.

Formula I:

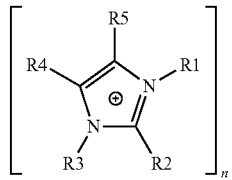

where
R1 and R3 are each an organic radical which is inert under the reaction conditions and has from 1 to 20 carbon atoms,
R2, R4 and R5 are each an H atom or an organic radical which is inert under the reaction conditions and has from 1 to 20 carbon atoms,
and n is 1, 2 or 3.

In formula I, preference is given to R1 and R3 each being, independently of one another, an organic radical which is inert under the reaction conditions and has from 1 to 10 carbon atoms. In particular, R1 and R3 are each an aliphatic, araliphatic or aromatic radical, in particular an aliphatic, araliphatic or aromatic radical having no further heteroatoms, e.g. an alkyl group. Particular preference is given to R1 and R3 each being, independently of one another, a straight-chain or branched $C_1$-$C_{10}$-alkyl group, for example a $C_1$-$C_4$-alkyl group such as methyl, ethyl, propyl, butyl, isobutyl.

In formula I, preference is given to R2, R4 and R5 each being, independently of one another, an H atom or an organic radical having from 1 to 10 carbon atoms; in particular, R2, R4 and R5 are each an H atom or an aliphatic, araliphatic or aromatic radical. Particular preference is given to R2, R4 and R5 each being, independently of one another, an H atom or an alkyl group; in particular, R2, R4 and R5 are each, independently of one another, an H atom or a straight-chain or branched $C_1$-$C_4$-alkyl group such as methyl, ethyl, propyl, butyl, isobutyl. Very particular preference is given to R2, R4 and R5 each being an H atom.

The ionic liquids can comprise inorganic or organic anions. Such anions are listed, for example, in WO 03/029329, WO 2007/076979, WO 2006/000197 and WO 2007/128268.

Possible anions are, in particular, anions selected from
the group of halides and halogen-comprising compounds of the formulae: $F^-$, $Cl^-$, $Br^-$, $I^-$, $BF_4^-$, $PF_6^-$, $AlCl_4^-$, $Al_2Cl_7^-$, $Al_3Cl_{10}^-$, $AlBr_4^-$, $FeCl_4^-$, $BCl_4^-$, $SbF_6^-$, $AsF_6^-$, $^-ZnCl_3^-$, $SnCl_3^-$, $CuCl_2^-$, $CF_3SO_3^-$, $C_4F_9SO_3^-$, $C_8F_{17}SO_3^-$, $(CF_3SO_3)_2N^-$, $(C_2F_5SO_2)_2N^-$, $CF_3CO_2^-$, $CCl_3CO_2^-$, $CN^-$, $SCN^-$, $OCN^-$, $NO^{2-}$, $NO^{3-}$, $N(CN)^-$;
the group of sulfates, sulfites and sulfonates of the general formulae: $SO_4^{2-}$, $HSO_4^-$, $SO_3^{2-}$, $HSO_3^-$, $R^aOSO_3^-$, $R^aSO_3^-$;
the group of phosphates of the general formulae: $PO_4^{3-}$, $HPO_4^{2-}$, $H_2PO_4^-$, $R^aPO_4^{2-}$, $HR^aPO_4^-$, $R^aR^bPO_4^-$;
the group of phosphonates and phosphinates of the general formulae: $R^aHPO_3^-$, $R^aR^bPO_2^-$, $R^aR^bPO_3^-$;
the group of phosphites of the general formulae: $PO_3^{3-}$, $HPO_3^{2-}$, $H_2PO_3^-$, $R^aPO_3^{2-}$, $R^aHPO_3^-$, $R^aR^bPO_3^-$;
the group of phosphonites and phosphinites of the general formulae: $R^aR^bPO_2^-$, $R^aHPO_2^-$, $R^aR^bPO^-$, $R^aHPO^-$;
the group of carboxylates of the general formula: $R^aCOO^-$;
the group of borates of the general formulae: $BO_3^{3-}$, $HBO_3^{2-}$, $H_2BO_3^-$, $R^aR^bBO_3^-$, $R^aHBO_3^-$, $R^aBO_3^{2-}$, $B(OR^a)(OR^b)(OR^c)(OR^d)^-$, $B(HSO_4)^-$, $B(R^aSO4)^-$;
the group of boronates of the general formulae: $R^aBO_2^{2-}$, $R^aR^bBO^-$;
the group of carbonates and carbonic esters of the general formulae: $HCO_3^-$, $CO_3^{2-}$, $R^aCO_3^-$;
the group of silicates and silicic esters of the general formulae: $SiO_4^{4-}$, $HSiO_4^{3-}$, $H_2SiO_4^{2-}$, $H_3SiO_4^-$, $R^aSiO_4^{3-}$, $R^aR^bSiO_4^{2-}$, $R^aR^bR^cSiO_4^-$, $HR^aSiO_4^{2-}$, $H_2R^aSiO_4^-$, $HR^aR^bSiO_4^-$;
the group of alkyl silane and aryl silane salts of the general formulae: $R^aSiO_3^{3-}$, $R^aR^bSiO_2^{2-}$, $R^aR^bR^cSiO^-$, $R^aR^bR^cSiO_3^-$, $R^aR^bR^cSiO_2^-$, $R^aR^bSiO_3^{2-}$;
the group of carboximides, bis(sulfonyl)imides and sulfonylimides of the general formulae:

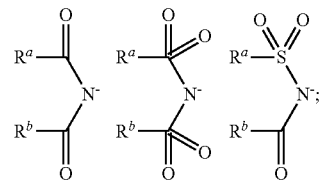

the group of methanides of the general formula:

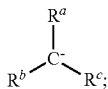

the group of halometalates of the general formula: $[M_rHal_t]^{s-}$,
  where M is a metal and Hal is fluorine, chlorine, bromine or iodine, r and t are positive integers and indicate the stoichiometry of the complex and s is a positive integer and indicates the charge on the complex;
the group of sulfides, hydrogensulfides, polysulfides, hydrogenpolysulfides and thiolates of the general formulae: $S^{2-}$, $HS^-$, $[S_v]^{2-}$, $[HS_v]^-$, $[R^aS]^-$,
  where v is a positive integer from 2 to 10; and
the group of complex metal ions such as $Fe(CN)_6^{3-}$, $Fe(CN)_6^{4-}$, $MnO_4^-$, $Fe(CO)_4^-$.

In the above anions, $R^a$, $R^b$, $R^c$ and $R^d$ are each, independently of one another,
hydrogen;
$C_1$-$C_{30}$-alkyl and aryl-, heteroaryl-, cycloalkyl-, halogen-, hydroxy-, amino-, carboxy-, —O—, —CO—O— or —CO—N<substituted derivatives thereof, for example methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, phenylmethyl (benzyl), diphenylmethyl, triphenylmethyl, 2-phenylethyl, 3-phenylpropyl, cyclopentylmethyl, 2-cyclopentylethyl, 3-cyclopentylpropyl, cyclohexylmethyl, 2-cyclohexylethyl, 3-cyclohexylpropyl, methoxy, ethoxy, acetyl or $C_qF_{2(q-a)+(1-b)}H_{2a+b}$ where $q \leq 30$, $0 \leq a \leq q$ and $b = 0$ or 1 (for example $CF_3$, $C_2F_5$, $CH_2CH_2$—$C_{(q-2)}F_{2(q-2)+1}$, $C_6F_{13}$, $C_8F_{17}$, $C_{10}F_{21}$, $C_{12}F_{25}$);
$C_3$-$C_{12}$-cycloalkyl and aryl-, heteroaryl-, cycloalkyl-, halogen-, hydroxy-, amino-, carboxy-, —O— or —CO—O-substituted derivatives thereof, for example cyclopentyl, 2-methyl-1-cyclopentyl, 3-methyl-1-cyclopentyl, cyclohexyl, 2-methyl-1-cyclohexyl, 3-methyl-1-cyclohexyl, 4-methyl-1-cyclohexyl or $C_qF_{2(q-a)-(1-b)}H_{2a-b}$ where $q \leq 30$, $0 \leq a \leq q$ and $b = 0$ or 1,
$C_2$-$C_{30}$-alkenyl and aryl-, heteroaryl-, cycloalkyl-, halogen-, hydroxy-, amino-, carboxy-, —O—, or —CO—O-substituted derivatives thereof, for example 2-propenyl, 3-butenyl, cis-2-butenyl, trans-2-butenyl or $C_qF_{2(q-a)-(1-b)}H$ where $q \leq 30$, $0 \leq a \leq q$ and $b = 0$ or 1;
$C_3$-$C_{12}$-cycloalkenyl and aryl-, heteroaryl-, cycloalkyl-, halogen-, hydroxy-, amino-, carboxy-, —O—, or —CO—O-substituted derivatives thereof, for example 3-cyclopentenyl, 2-cyclohexenyl, 3-cyclohexenyl, 2,5-cyclohexadienyl or $C_qF_{2(q-a)-3(1-b)}H_{2a-3b}$ where $q \leq 30$, $0 \leq a \leq q$ and $b = 0$ or 1;

aryl or heteroaryl having from 2 to 30 carbon atoms and alkyl-, aryl-, heteroaryl-, cycloalkyl-, halogen-, hydroxy-, amino-, carboxy-, —O—, or —CO—O-substituted derivatives thereof, for example phenyl, 2-methylphenyl (2-tolyl), 3-methylphenyl (3-tolyl), 4-methylphenyl, 2-ethylphenyl, 3-ethylphenyl, 4-ethylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 4-phenylphenyl, 1-naphthyl, 2-naphthyl, 1-pyrrolyl, 2-pyrrolyl, 3-pyrrolyl, 2-pyridinyl, 3-pyridinyl, 4-pyridinyl or $C_6F_{(5-a)}H_a$ where $0 \leq a \leq 5$; or
two radicals form an unsaturated, saturated or aromatic ring which is optionally substituted by functional groups, aryl, alkyl, aryloxy, alkyloxy, halogen, heteroatoms and/or heterocycles and optionally interrupted by one or more oxygen and/or sulfur atoms and/or one or more substituted or unsubstituted imino groups.

In the above anions, preference is given to $R^a$, $R^b$, $R^c$ and $R^d$ each being, independently of one another, a hydrogen atom or a $C_1$-$C_{12}$-alkyl group.

Mention may be made by way of example of the following anions: chloride; bromide; iodide; thiocyanate; hexafluorophosphate; trifluoromethanesulfonate (triflate); methanesulfonate; carboxylates, in particular formate; acetate; mandelate; nitrate; nitrite; trifluoroacetate; sulfate; hydrogensulfate; methylsulfate; ethylsulfate; 1-propylsulfate; 1-butylsulfate; 1-hexylsulfate; 1-octylsulfate; phosphate; dihydrogenphosphate; hydrogenphosphate; $C_1$-$C_4$-dialkylphosphates; propionate; tetrachloroaluminate; $Al_2Cl_7^-$; chlorozincate; chloroferrate; bis(trifluoromethyl-sulfonyl)imide; bis(pentafluoroethylsulfonyl)imide; bis(nonafluorobutylsulfonyl)imide, bis(heptadecafluorooctylsulfonyl)imide, bis(methylsulfonyl)imide; bis(p-tolylsulfonyl)imide; tris(trifluoromethylsulfonyl)methanide; bis(pentafluoroethylsulfonyl)methanide; p-toluenesulfonate; tetracarbonylcobaltate; dimethylene glycol monomethyl ether sulfate; oleate; stearate; acrylate; methacrylate; maleate; hydrogencitrate; vinylphosphonate; bis(pentafluoro-ethyl)phosphinate; borates such as bis[salicylato(2-)]borate, bis[oxalato(2-)]borate, bis[1,2-benzenediolato(2-)—O,O']borate, tetracyanoborate, tetrafluoroborate; dicyanamide; tris(pentafluoroethyl)trifluorophosphate; tris(heptafluoropropyl) trifluorophosphate, hexafluorophosphate, cyclic arylphosphates such as catecholphosphate $(C_6H_4O_2)P(O)O$— and chlorocobaltate.

Preferred anions are those from the group consisting of
alkylsulfates $R^aOSO_3^-$, where $R^a$ is a $C_1$-$C_{12}$-alkyl group, preferably a $C_1$-$C_6$-alkyl group,
alkylsulfonates $R^aSO_3^-$; where $R^a$ is a $C_1$-$C_{12}$-alkyl group, preferably a $C_1$-$C_6$-alkyl group,
arylsulfonates $R^aSO_3^-$; where $R^a$ is an aromatic which is substituted by a $C_1$-$C_{12}$-alkyl group, preferably substituted by a $C_1$-$C_6$-alkyl group,
perfluorinated sulfonates $R^aSO_3^-$; where $R^a$ is a $C_1$-$C_{12}$-alkyl group which is perfluorinated, preferably a $C_1$-$C_6$-alkyl group which is perfluorinated,
halides, in particular chloride and bromide, and
pseudohalides, such as thiocyanate, dicyanamide,
carboxylates $R^aCOO$—; where $R^a$ is a $C_1$-$C_{20}$-alkyl group, preferably a $C_1$-$C_8$-alkyl group, in particular acetate,
phosphates, in particular dialkylphosphates of the formula $R^aR^bPO_4^-$, where $R^a$ and $R^b$ are each, independently of one another, a $C_1$-$C_6$-alkyl group; in particular, $R^a$ and $R^b$ are the same alkyl group, with mention being able to be made of dimethylphosphate and diethylphosphate, perfluorinated phosphates such as tris(pentafluoroethyl) trifluorophosphate; tris(heptafluoropropyl)trifluorophosphate, hexafluorophosphate, phosphonates, in particular the monoalkylphosphonic esters of the formula $R^aR^bPO_3^-$, where $R^a$ and $R^b$ are each, independently of one another, a $C_1$-$C_6$-alkyl group, perfluorinated phosphinates, in particular the perfluorinated monoalkylphosphinic esters of the formula $R^aR^bPO_2^-$, where $R^a$ and $R^b$ are each, independently of one another, a $C_1$-$C_6$-alkyl group, e.g. bis(pentafluoroethyl)phosphinate, perfluorinated sulfonylimides such as bis(trifluoromethylsulfonyl)imide; bis(pentafluoroethylsulfonyl)imide; bis(nonafluorobutylsulfonyl)imide, bis(heptadecafluorooctylsulfonyl)imide, methanides such as tricyanomethanide, perfluorinated sulfonylmethanides, such as tris(trifluoromethylsulfonyl)methanide, bis(pentafluoroethylsulfonyl)methanide, $BF_4$.

Particularly preferred anions are chloride, bromide, hydrogensulfate, tetrachloroaluminate, thiocyanate, dicyanamide, tricyanomethanide, methylsulfate, ethylsulfate, methanesulfonate, trifluoromethanesulfonate, nonafluorobutanesulfonate, formate, acetate, dimethylphosphate, diethylphosphate, p-toluenesulfonate, tetrafluoroborate and hexafluorophosphate, methylmethanephosphonate, methylphosphonate, and bis(trifluoromethylsulfonyl)imide.

The abovementioned cations and anions combine to form salts which are preferably ionic liquids. Particular preference is given to imidazolium salts of the formula II below, where the cation has the properties described for formula I:

Formula II:

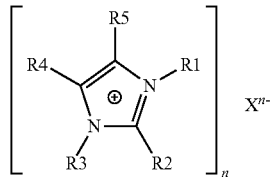

where

R1 and R3 are each an organic radical which is inert under the reaction conditions and has from 1 to 20 carbon atoms, R2, R4 and R5 are each an H atom or an organic radical which is inert under the reaction conditions and has from 1 to 20 carbon atoms, X is an anion and n is 1, 2 or 3.

In formula II, X is an anion, preferably one of the abovementioned anions.

A person skilled in the art will also subdivide the class of ionic liquids according to their miscibility with water into hydrophobic and hydrophilic ionic liquids, which are generally also weakly to strongly hydroscopic. A miscibility gap with water allows a two-phase reaction in the presence of water. The solubility of water in a hydrophobic ionic liquid is (under normal conditions, i.e. 20° C., 1 bar) less than 100 g of water in 1000 g of ionic liquid, preferably less than 50 g, particularly preferably less than 25 g, in particular less than 10 g. The hydrophobic character of the ionic liquids can be achieved, for example by halogenation, especially by means of a high degree of fluorination, for example perfluorination, of the anion.

Very particularly preferred anions in formula II are accordingly those which make the ionic liquid hydrophobic, for example perfluorinated sulfonates (e.g. $C_4F_9SO_3^-$, $C_8F_{17}SO_3^-$), perfluorinated sulfonylimides (e.g. bis(trifluoromethylsulfonyl)imide, bis(pentafluoroethylsulfonyl)imide, bis(nonafluorobutylsulfonyl)imide, bis(heptadecafluorooctylsulfonyl)imide), perfluorinated phosphinates (e.g. bis(pentafluoroethyl)phosphinate), perfluorinated phosphates (e.g. tris(pentafluoroethyl)trifluorophosphate; tris(heptafluoropropyl)trifluorophosphate, hexafluorophosphate). Particular preference is given to bis(trifluoromethylsulfonyl)imide.

In formula II, n is preferably 1.

Particularly preferred ionic liquids consist exclusively of an organic cation with one of the above anions.

The molecular weight of the ionic liquids is generally less than 2000 g/mol, particularly preferably less than 1500 g/mol, particularly preferably less than 1000 g/mol and very particularly preferably less than 750 g/mol.

Ionic liquids can be applied to support materials. Bonding to a support surface can be effected by means of:

covalent bonding between silanol groups and the anion or cation of the ionic liquid, noncovalent bonding in the form of physisorption via van der Waals and dipole forces.

According to the invention, catalysts in which ionic liquids are bound noncovalently to a support are used.

Possible supports are, for example, aluminum oxide, titanium dioxide, zirconium dioxide, silicon dioxide, magnesium dioxide, individually or in combination (e.g. silicon oxide/aluminum oxide, silicon oxide/titanium dioxide, silicon dioxide/zirconium dioxide, magnesium oxide/aluminum oxide, titanium dioxide/zirconium dioxide) or else zeolites, activated carbons or polymers. The supports can be used in all known modifications; for example, catalysts can be produced on the basis of $\gamma$-$Al_2O_3$, $\theta$-$Al_2O_3$ or $\alpha$-$Al_2O_3$, on the basis of monoclinic, tetragonal or cubic $ZrO_2$, on the basis of $TiO_2$ in the rutile or anatase modification.

The support materials can have pores, e.g. can have a pore volume of from 0.05 to 1.0 ml/g.

The supported catalysts used according to the invention can be used either alone or in combination with a further catalytically active substance.

As catalytically active substances, it is possible to add substances, in particular acids, to the ionic liquids. Particular preference is given to adding Lewis acids such as an aluminum, scandium, indium, zinc, iron or copper halide, trifluoromethanesulfonate or oxide. The content of Lewis acid which can be added to the ionic liquid is preferably 0.1-50% by weight, more preferably 0.1-10% by weight, particularly preferably less than 5% by weight, in each case based on the total supported catalyst.

The catalytically active phase can comprise further solvents in addition to the ionic liquid, e.g. in order to control the flow properties of the catalytically active phase. When selecting the solvent, it should be ensured that this does not react with the ionic liquid or any Lewis acid additionally present and in this way chemically change the catalytically active phase. The solvent used should remain unchanged in the catalytically active phase in the process of the invention. For this reason, the chosen reaction conditions have to be taken into account when selecting the solvent. For example, the reaction temperatures will be chosen so that the solvent is not lost by evaporation in the process of the invention. Preference is given to solvents having boiling points which are greater than the reaction temperature. For example, polyethylene glycols, e.g. PEG 400 or PEG 600, can be used.

The supported ionic liquid phase catalysts are produced by methods known to those skilled in the art (for example Topics in Catalysis (1991), 14(1-4), 139-44 or Green Chemistry (2002), 4, 88-93). In particular, the supported catalyst should be dried before immobilization of the ionic liquid or the ionic liquid/Lewis acid mixture on the supported catalyst. The SILP catalyst is preferably produced under a protected gas atmosphere.

The content of ionic liquid phase catalyst applied to the support material is preferably 10-50% by weight, particularly preferably 10-25% by weight, in each case based on the total supported catalyst.

The supported ionic liquid phase catalysts can, (depending on the supported catalyst used) be used in the form of powder or preferably in the form of shaped bodies such as extrudates, crushed material, rings, hollow cylinders, spheres or pellets, for example bodies having a diameter of from 0.1 to 5 mm, preferably from 1 to 3 mm. Binders can be added to the catalyst for the production of shaped bodies.

The reaction according to the invention in the gas phase using supported ionic liquid phase catalysts, which can in particular also be carried out in the presence of water, will be described below.

In the reaction according to the invention, aldehydes or ketones are added electrophilically onto an alkene, followed by addition of a nucleophile onto the resulting intermediate, so that a homoallyl alcohol is obtained selectively as reaction product.

For the purposes of the present invention, an alkene is an unsubstituted or substituted aliphatic alkene. An aliphatic alkene is a straight-chain, branched or cyclic alkene which preferably has from 3 to 20 carbon atoms. Such an alkene is described as substituted when it bears one or more inert radicals such as phenyl, cyclopentyl or cyclohexyl.

Unsubstituted aliphatic alkenes having from 3 to 20 carbon atoms preferably serve as starting materials. In a preferred embodiment, a straight-chain or branched $C_3$-$C_6$-alkene such as propene, butene, isobutene, pentene or hexene serves as starting material.

For the purposes of the present invention, an aldehyde is an aliphatic aldehyde or an aromatic aldehyde. An aliphatic aldehyde is a straight-chain, branched or cyclic aldehyde which preferably has from 1 to 20 carbon atoms, particularly preferably from 1 to 10 carbon atoms, in particular from 1 to 4 carbon atoms, with the alkyl chains being able to be unsubstituted or substituted by groups which are inert under the reaction conditions. Such inert groups are, for example, aryl groups such as phenyl or phenyl substituted by alkyl, preferably alkyl having from 1 to 4 carbon atoms, e.g. methyl, ethyl, isopropyl, butyl, isobutyl, by alkoxy, preferably alkoxy having from 1 to 4 carbon atoms, e.g. methoxy, ethoxy, propoxy, butoxy or by halogen.

Aromatic aldehydes are aldehydes in which one or more aldehyde groups are bound directly to an aromatic carbon atom, for example in a phenyl, naphthyl, or pyridyl group, e.g. benzaldehyde, phthalaldehyde, naphthyl aldehydes, pyridyl aldehyde or dialdehyde.

For the purposes of the present invention, a ketone is an aliphatic ketone or an aromatic ketone. An aliphatic ketone is a straight-chain, branched or cyclic ketone which preferably has from 3 to 20 carbon atoms, particularly preferably from 3 to 10 carbon atoms, with the alkyl chains being able to be unsubstituted or substituted by groups which are inert under the reaction conditions. Such inert groups are, for example, aryl groups such as phenyl or phenyl substituted by alkyl, preferably alkyl having from 1 to 4 carbon atoms, e.g. methyl, ethyl, isopropyl, butyl, isobutyl, by alkoxy, preferably alkoxy having from 1 to 4 carbon atoms, e.g. methoxy, ethoxy, propoxy, butoxy or by halogen.

Aromatic ketones are ketones in which a keto group is bound directly to at least one aromatic carbon atom, for example to a phenyl, naphthyl or pyridyl group. The second bonding position is then occupied by an aliphatic carbon atom which is alkyl, preferably alkyl having from 1 to 6 carbon atoms, particularly preferably from 1 to 4 carbon atoms, e.g. methyl, ethyl, isopropyl, butyl, neopentyl, hexyl, for example methyl phenyl ketone. The keto group can also be bound to two aromatic carbon atoms, e.g. benzophenone.

Preference is given to using unsubstituted, aliphatic aldehydes having from 1 to 10 carbon atoms. The reaction is particularly preferably carried out using aliphatic $C_1$-$C_4$-aldehydes, for example formaldehyde, acetaldehyde, propionaldehyde. The reaction is very particularly preferably carried out using formaldehyde.

The reaction is preferably carried out using an excess of alkene. The excess can be very large (10-20-fold molar excess based on the aldehyde used or the ketone used). Preference is given to a 15-fold excess based on the aldehyde used, particularly preferably a 10-fold excess, very particularly preferably a less than 5-fold excess. In a particular embodiment, the unconsumed excess is recirculated to the system.

The reaction is carried out with the aid of the above-described catalyst systems. This makes it possible, in particular, to carry out the reaction using aqueous formaldehyde.

The reaction temperature is generally from ≥50° C. to not more than 350° C. Preference is given to the ranges 100-300° C., particularly preferably 100-250° C., very particularly preferably 100-200° C. The reaction temperature is selected so that it is in the range of the thermal stability of the ionic liquid, which is dependent on the choice of ionic liquid and can be assessed by a person skilled in the art.

The reaction can be carried out under subatmospheric pressure (<1 bar), at atmospheric pressure (=1 bar) or under superatmospheric pressure (>1 bar). It is preferably carried out in the region of atmospheric pressure.

The reaction can be carried out batchwise or continuously, preferably continuously.

The reaction products are isolated in a conventional way, in the case of isoprenol by, for example, condensation. Further purification can be effected by, for example, distillation.

EXAMPLES (1) Catalyst Production 3.1 g of $AlCl_3$ (Lewis acid) were dissolved in 27.9 g of EMIM TFSI (1-ethyl-3-methylimidazolium bis(trifluoromethylsulfonyl)imide; ionic liquid). 61.8 g of D11-10® 3 mm extrudates ($SiO_2$; support material) were subsequently suspended in 100 g of dichloromethane (organic solvent) and admixed with the $AlCl_3$/EMIM TFSI mixture. The suspension was stirred and the solvent was subsequently removed under reduced pressure. This left 91.3 g of supported ionic liquid phase catalyst.

(2) Gas-phase Reaction 48 g of catalyst (crushed D11-10® loaded with 50% by weight of EMIM TFSI and 10% by weight of $AlCl_3$ based on the total supported catalyst) were installed in the gas-phase apparatus. At a reaction temperature of 150° C., 10 g/h (0.12 mol/h) of 36.5% strength formaldehyde solution (0.2 g/g of Cat/h), 5.4 standard liters/h (0.24 mol/h) of isobutene (introduced in gaseous form from a gas bottle) and 2 standard liters/h of $N_2$ were passed through the apparatus. After a period of operation of 8 hours, the reaction output (condensed by means of a condenser and a cold trap at 0° C.) comprised isoprenol and isoprene in a ratio of 26.53:1.37 GC-% by area at an isobutene conversion of 5%.

The invention claimed is:

1. A process for preparing homoallyl alcohols by catalyzed reaction of alkenes with aldehydes or ketones, wherein the reaction is carried out in the gas phase in the presence of noncovalently supported ionic liquid phase catalysts.

2. The process according to claim 1, wherein aqueous formaldehyde is used as aldehyde.

3. The process according to claim 1, wherein the reaction is carried out in the presence of a Lewis acid.

4. The process according to claim 1, wherein the catalyst is an imidazolium salt.

5. The process according to claim 1, wherein the catalyst is hydrophobic.

6. The process according to claim 5, wherein the catalyst comprises a perfluorinated anion.

7. The process according to claim 1, wherein aliphatic alkenes having from 3 to 20 carbon atoms are reacted with aqueous formaldehyde.

8. The process according to claim 1, wherein isobutene is reacted with aqueous formaldehyde.

9. The process according to claim 1, wherein the process is carried out at temperatures of from ≥50° C. to not more than 350° C.

10. The process according to claim 1, wherein the alkene is used in a 10-20-fold molar excess based on the aldehyde or the ketone.

* * * * *